(12) United States Patent
Alshemari

(10) Patent No.: US 8,382,777 B1  
(45) Date of Patent: Feb. 26, 2013

(54) SURGICAL NEEDLE HOLDER

(76) Inventor: Hasan M. Sh. Sh. Alshemari, Saad Al Abdulla (KW)

( * ) Notice: Subject to any disclaimer, the term of this patent is extended or adjusted under 35 U.S.C. 154(b) by 0 days.

(21) Appl. No.: 13/586,271

(22) Filed: Aug. 15, 2012

Related U.S. Application Data (63) Continuation of application No. 13/356,498, filed on Jan. 23, 2012.

(51) Int. Cl.
*A61B 17/04* (2006.01)

(52) U.S. Cl. .................. 606/148; 606/205; 606/208

(58) Field of Classification Search .............. 606/148, 606/208; 433/4, 157, 159, 160
See application file for complete search history.

(56) References Cited

U.S. PATENT DOCUMENTS

| | | | | |
|---|---|---|---|---|
| 4,130,938 | A * | 12/1978 | Uhlmann | 30/192 |
| 5,176,699 | A * | 1/1993 | Markham | 606/206 |
| 5,275,615 | A * | 1/1994 | Rose | 606/208 |
| 5,282,806 | A * | 2/1994 | Haber et al. | 606/139 |
| 5,632,746 | A * | 5/1997 | Middleman et al. | 606/78 |
| 7,494,501 | B2 * | 2/2009 | Ahlberg et al. | 606/207 |
| 7,942,895 | B2 * | 5/2011 | Jinno et al. | 606/205 |
| 8,182,478 | B2 * | 5/2012 | Bartel | 606/37 |

OTHER PUBLICATIONS

Prior art cited in parent U.S. Appl. No. 13/356,498, filed Jan. 23, 2012, the priority of which is claimed herein.

* cited by examiner

*Primary Examiner* — Corrine M McDermott
*Assistant Examiner* — Todd J Scherbel
(74) *Attorney, Agent, or Firm* — Richard C. Litman (57) ABSTRACT

The surgical needle holder has two elongated arms that end in expansions in the form of scissor finger loops for introducing the fingers and correspondingly actuating both arms. The elongated arms are pivotally attached to each other and have pivotally mounted jaws at the ends of the elongated arms. Bevel gear mechanisms interface the elongated arms with the pivotally mounted jaws so that separating the finger loops separates the jaws, and bringing the finger loops together closes the jaws to grip a surgical needle. The needle holder has ratchet lock members extending towards each other between the elongated arms in order to lock the jaws on the surgical needle, similar to the locking of a hemostat. By applying this gear configuration, the motion of needles will be along any plane parallel to the longitudinal axle of the device while the surgeon's hand is in a neutral position.

3 Claims, 10 Drawing Sheets

SURGICAL NEEDLE HOLDER

CROSS-REFERENCE TO RELATED APPLICATIONS

This is a continuation of my prior application Ser. No. 13/356,498, filed Jan. 23, 2012 now pending.

BACKGROUND OF THE INVENTION

1. Field of the Invention

The present invention relates generally to surgical instruments, and more particularly to a surgical needle holder that provides a holding and driving instrument for a suture needle.

2. Description of the Related Art

A needle holder, also called a needle driver, is a surgical instrument similar to a hemostat that is used by doctors and surgeons to hold a suturing needle for closing wounds during suturing and surgical procedures.

The parts of a simple needle holder are the jaws, the joint and the handles. Most needle holders also have a clamp mechanism that locks the needle in place, allowing the user to maneuver the needle through various tissues. To maintain a firm grip on the needle, the jaws are often textured and short compared to the handles, thereby increasing the applied force via the lever principle. With the simple needle holder, the handle portion and the jaws portion work together in-plane. One particular problem arises when the surgeon, from an ergonomic standpoint, needs to operate the jaws with his/her hand rotated 90° from the jaws action.

Thus, a surgical needle holder solving the aforementioned problems is desired.

SUMMARY OF THE INVENTION

The surgical needle holder has two elongated arms that end in expansions in the form of scissor finger loops for introducing the fingers and correspondingly actuating both arms. The elongated arms are pivotally attached to each other and have pivotally mounted jaws at the ends of the elongated arms. Bevel gear mechanisms interface the elongated arms with the pivotally mounted jaws so that separating the finger loops separates the jaws, and bringing the finger loops together closes the jaws to grip a surgical needle. The needle holder has ratchet lock members extending towards each other between the elongated arms in order to lock the jaws on the surgical needle, similar to the locking of a hemostat. The needle holder is preferably constructed of surgical stainless steel.

In this embodiment, the surgical needle holder is configured in such a manner as to manipulate and move needles along any plane parallel to the longitudinal axle of the device. By using two perpendicular planes of gear system, the related needle is grasped in a position to function while the operator's hand is in a neutral position. In such an embodiment, the needle automatically moves into an ideal position for straight vertical rather than elliptical motion. In other words, the needle is in a position to enter the tissue without any hand motion.

This provides the surgeon with an implement to facilitate driving a needle suture in difficult conditions of long reaching tissues or limited space, such as when reaching down into the abdomen or into the base of tongue, during which the surgeon is required to handle and manipulate these instruments in relatively small and sometimes minute increments and degrees. The gear system configuration in the needle holder will add more control of a suturing operation by increasing comfort the surgeon, steadiness of the surgeon's hand, and accuracy in the exact points of penetration.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
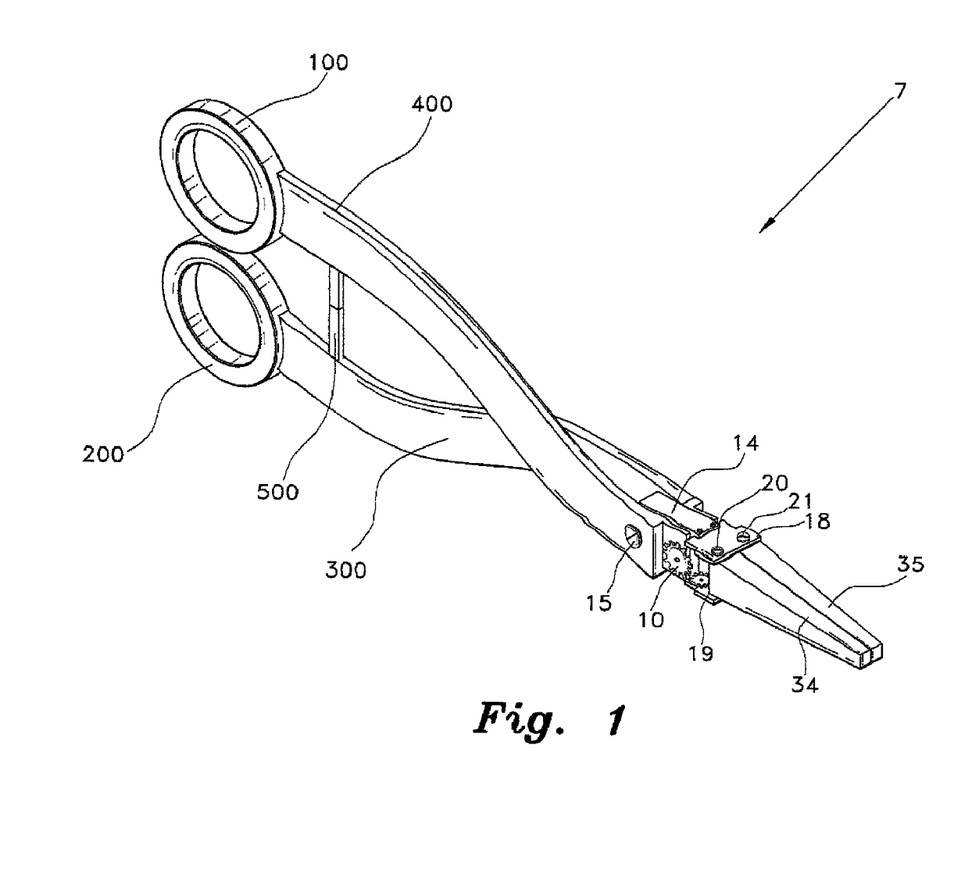
FIG. 1 is a perspective view of a surgical needle holder according to the present invention, shown in a closed position.
Figure 2:
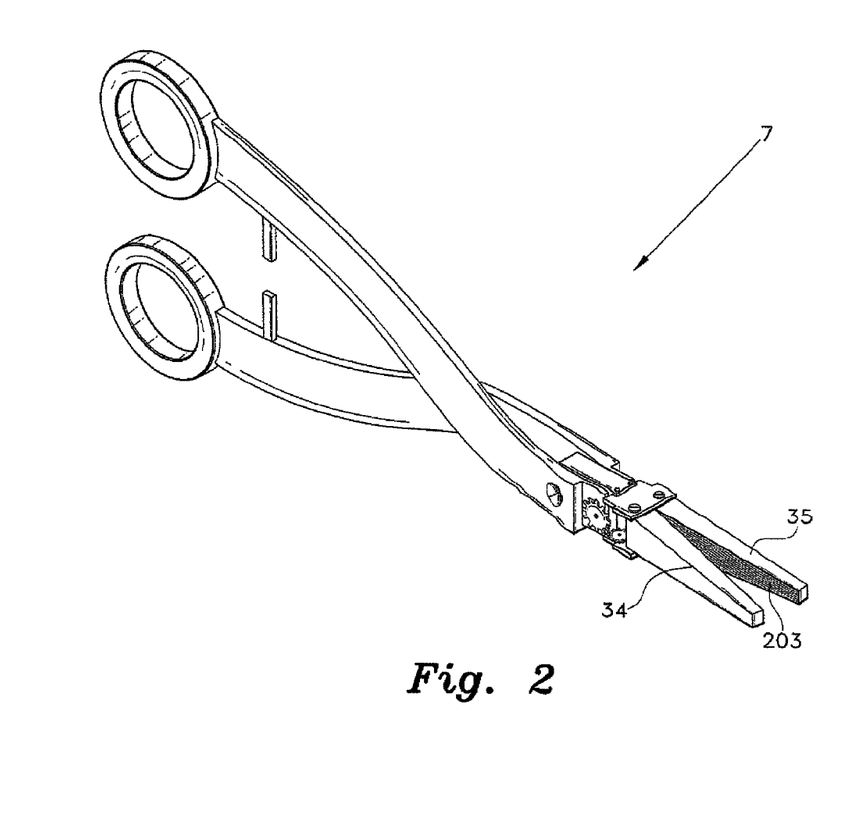
FIG. 2 is a perspective view of the surgical needle holder of FIG. 1, shown with the jaws in an open position.
Figure 5:
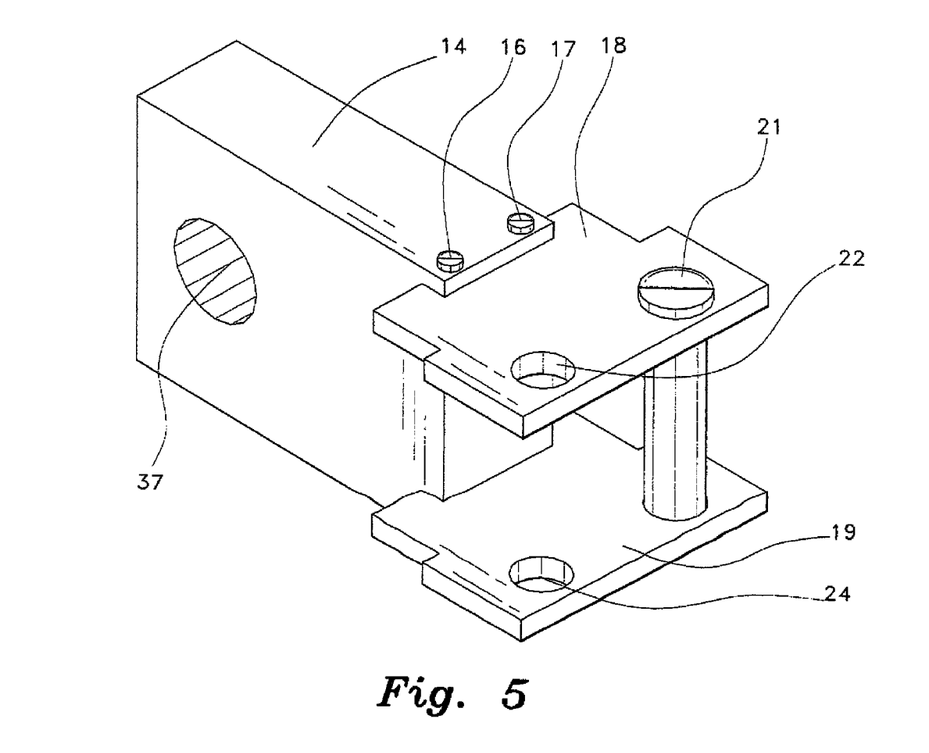
FIG. 5 is a perspective view of the center jaw mount of the surgical needle holder of FIG. 1, the arms and the jaws being omitted to show details thereof.

As shown in FIGS. 1 and 2, the surgical needle holder 7 comprises first and second elongate scissor arms 300, 400 that each extend on one end to form first and second scissor finger loops 200 and 100, respectively. The finger loops 200 and 100 are adapted for a user introducing fingers to manipulate the arms 300, 400. The elongate arms 300 and 400 are of equal length The finger grips 100, 200 of the elongate arms 400, 300 are coplanar. The two elongate arms 300 and 400 are bent crossing over each other in a non-coplanar manner, as shown, so that the ends distal from finger grips 100, 200 are non-coplanar and form a laterally extending pivot axis through which an axle 15 can be connected and secured by being disposed through a bore 37 (shown in. FIG. 5) of a retaining body 14 situated between the distal ends of the elongate arms 300 and 400.

Figure 3:
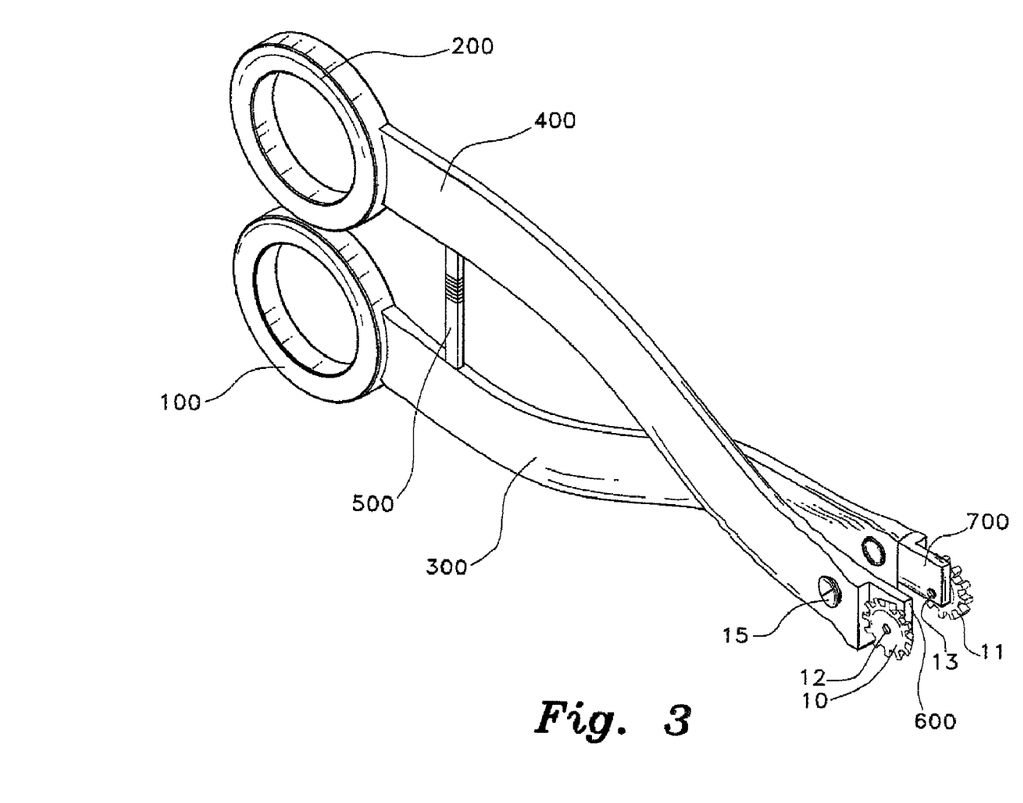
FIG. 3 is a perspective view of the elongated arms the surgical needle holder of FIG. 1, the jaws and center gear box being omitted to show details of the arms.
Figure 4:
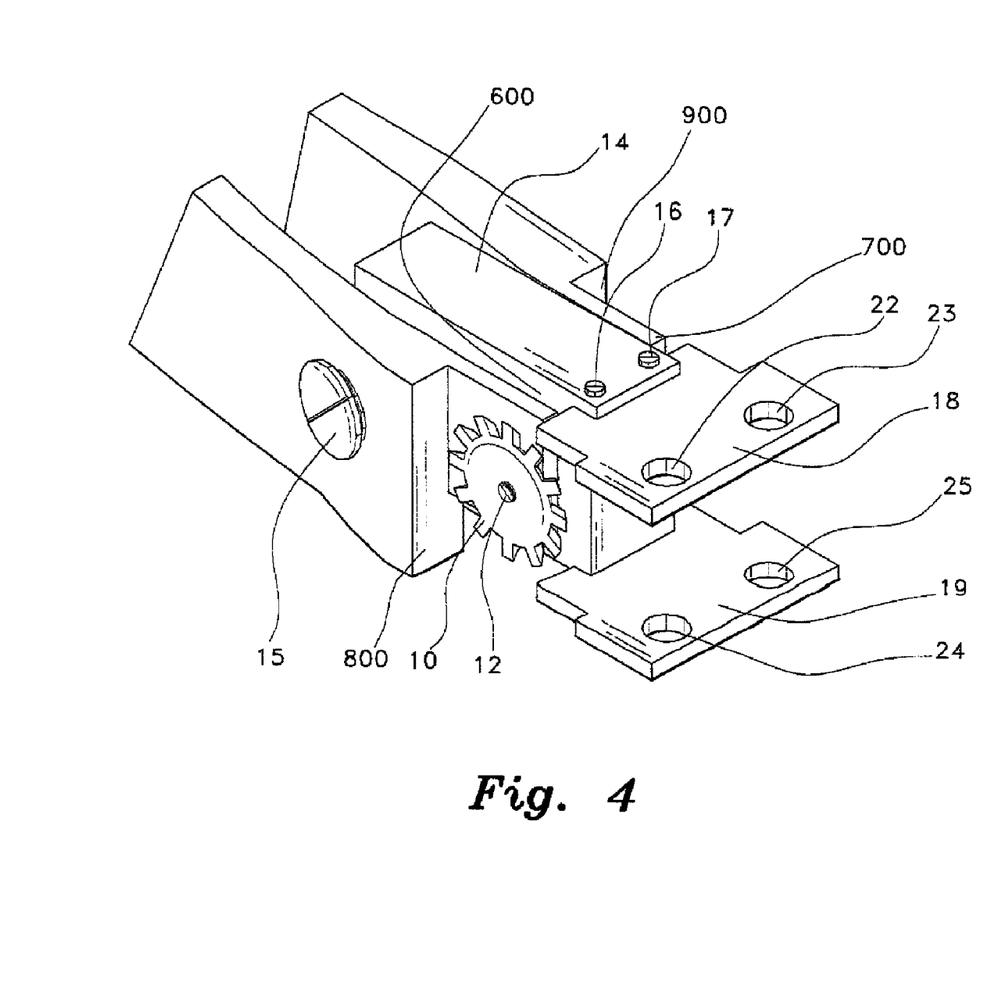
FIG. 4 is a partial perspective view of the surgical needle holder of FIG. 1, showing the center jaw mount between the distal ends of the elongated arms, the jaws and horizontal gear being omitted.
Figure 10:
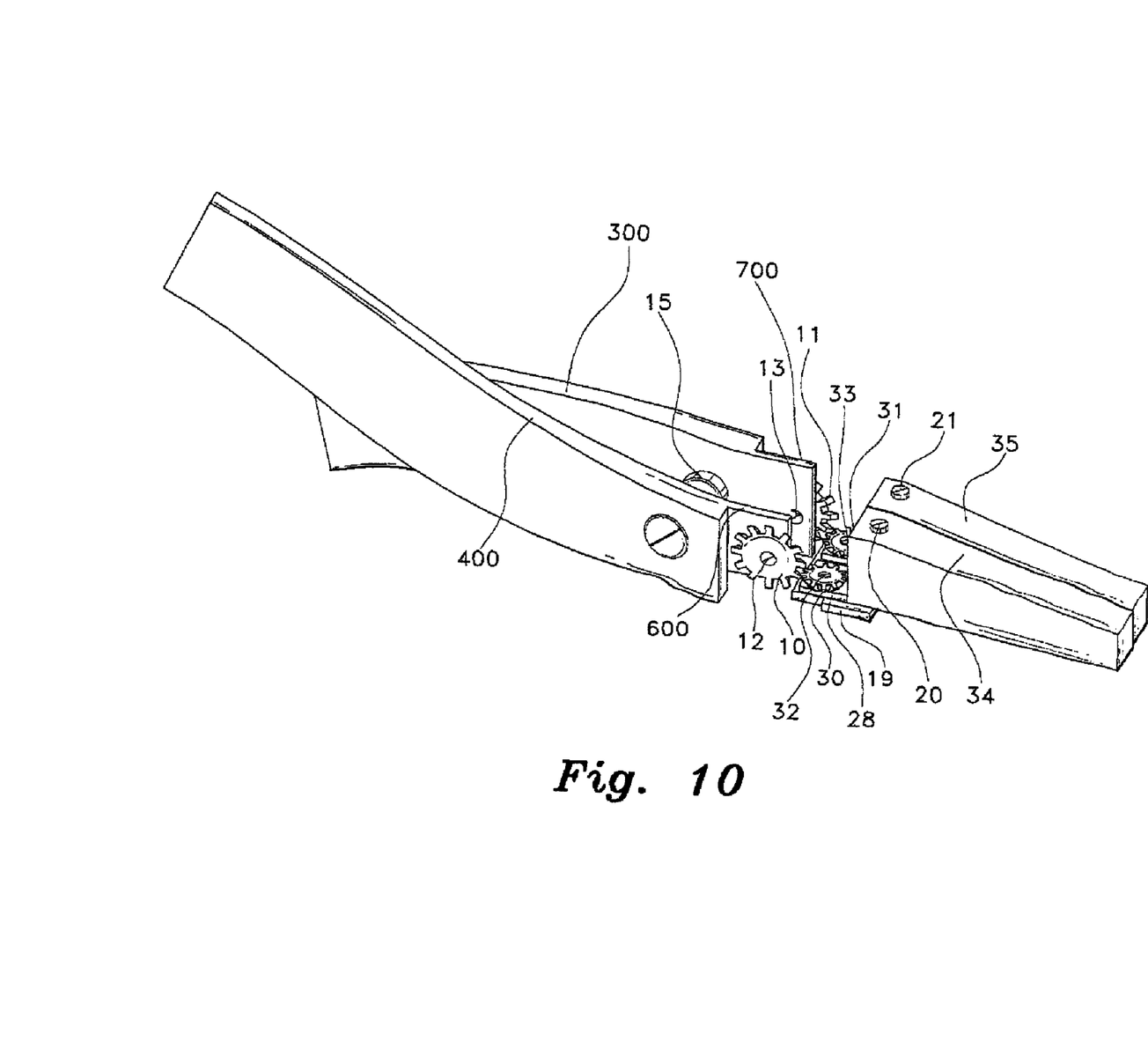
FIG. 10 is a partial perspective view of the surgical needle holder of FIG. 1, shown with the top plate of the jaw mount removed to show details of the gear mechanism.

As shown in FIGS. 3, 4 and 10, first and second elongate arm bevel gears 10 and 11 are attached to right and left ends of the elongate arms 300, 400 and are recessed in flat ends 600 and 700 that extend away and indent from end walls 800 and 900 of the respective elongate arms 400 and 300. The gears 10 and 11 are retained on gear shafts 12 and 13 rigidly attached to the flat ends 600 and 700. Scissor-like pivotal motion of the elongate arms 300, 400 along the laterally extending pivot axis defined by the axial center of the pivot axle 15 causes a gear mechanism partially defined by the first and second elongate arm bevel gears 10 and 11 to rotate.

Figure 6:
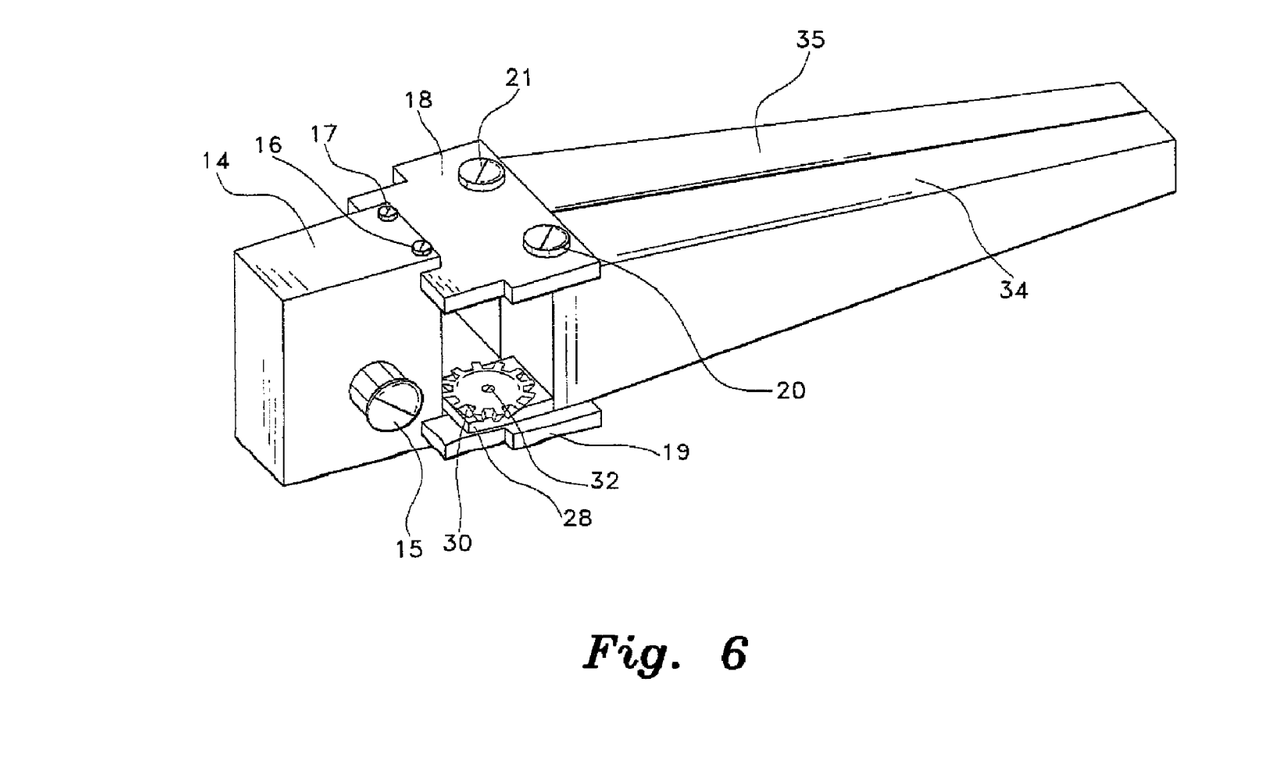
FIG. 6 is a rear perspective view of the center jaw mount of FIG. 5, showing the jaws attached thereto.
Figure 7:
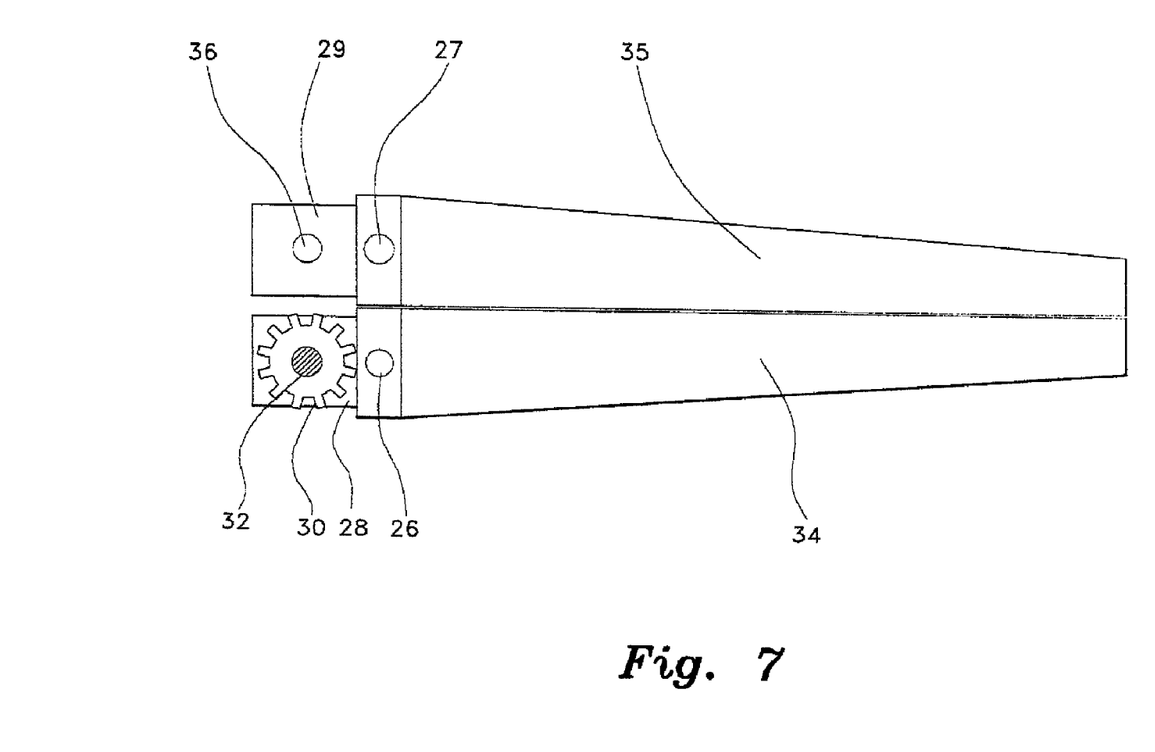
FIG. 7 is a top view of the jaws of the surgical needle holder of FIG. 1, the right-hand jaw having a horizontal gear attached thereto.

FIGS. 7, 8, 9 and 10 show that gripper beveled gears 30 and 31 are rigidly attached to elongate gripper jaws 34 and 35 at respective gripper jaw base plates 28 and 29 via fastener pins 32 and 33 (which serve as gear shafts) disposed through bores 36 and 37 of the gripper jaw base plates 28 and 29. The pins 32 and 33 may have keyed shafts, and the bores 36 and 37 may each have a corresponding keyway defined therein to assure rotation of the jaws 34, with the gripper beveled gears 30 and 31, if desired. The gripper jaw-gripper beveled gear assemblies are pivotally attached to the bottom plate 19 of a center jaw mount, the bottom plate 19 being attached to the bottom portion of the retaining body 14 of the center jaw mount. As shown in FIGS. 5 and 6, a notched top plate 18 is attached to the upper portion of the retaining body 14 of the center jaw mount, and extends away from the retaining body 14. Similarly, the notched bottom plate 19 is attached to the lower portion of the retaining body 14 and extends away from the retaining body 14. The top plate 18 and the bottom plate 19 may be secured to the retaining body 14 via pins 16 and 17.

Figure 8:
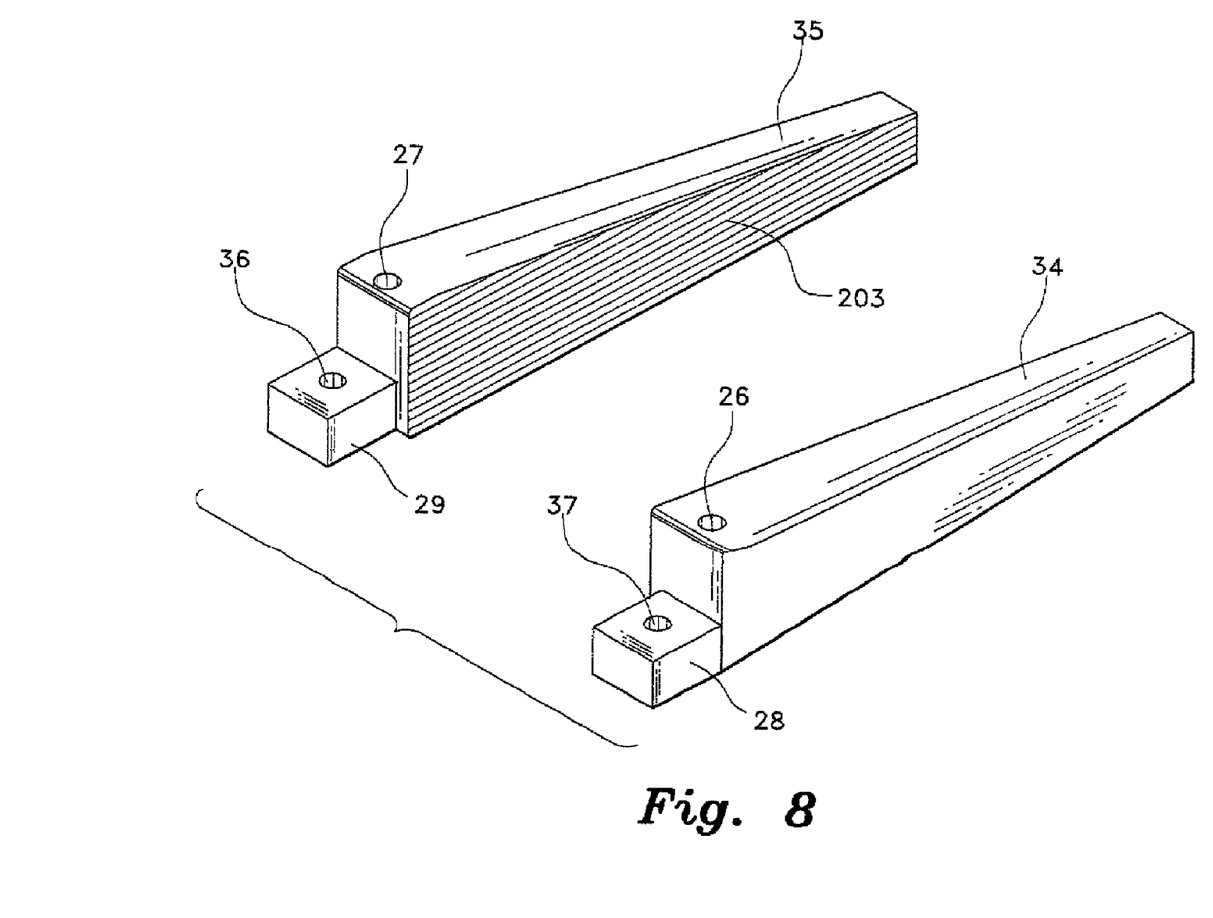
FIG. 8 is a rear perspective view of the left and right-hand jaws of the surgical needle holder of FIG. 1
Figure 9:
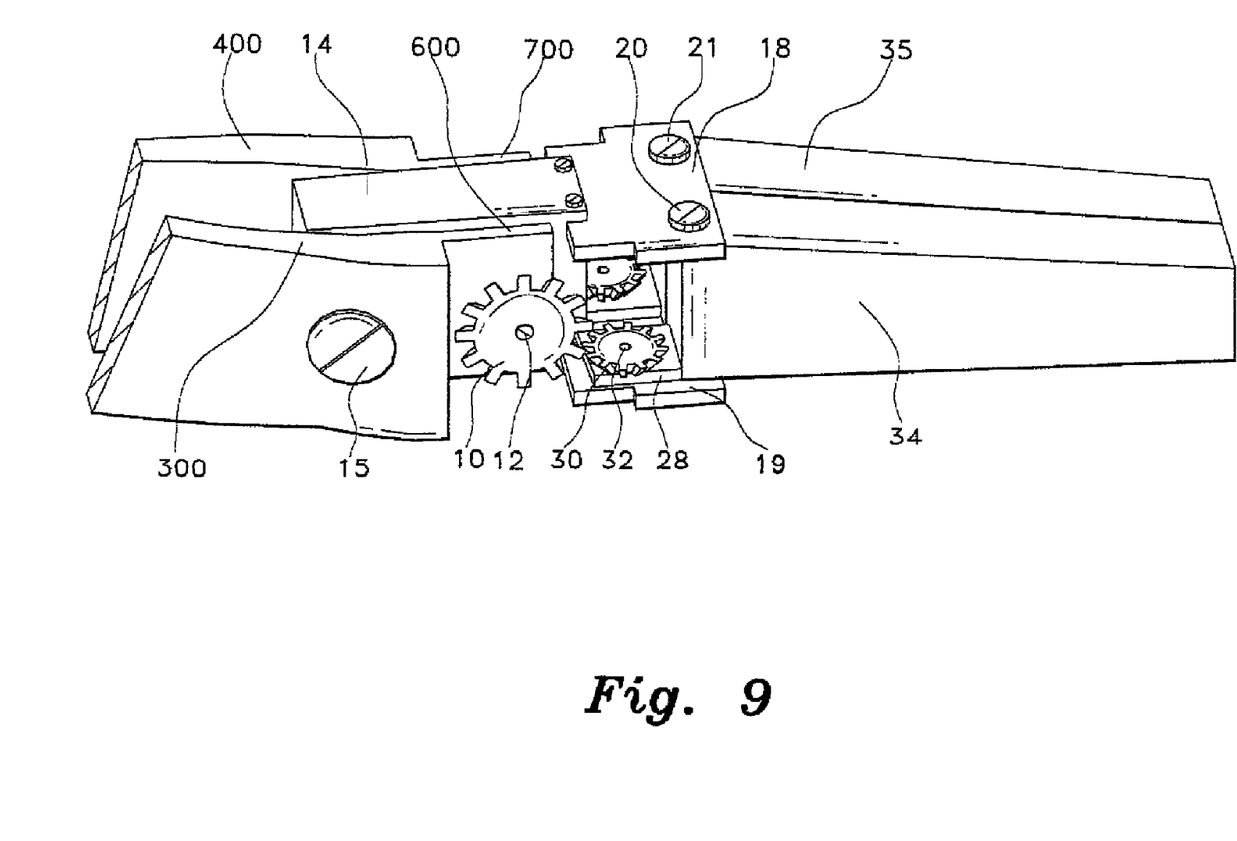
FIG. 9 is a partial perspective view of the surgical needle holder of FIG. 1, showing details of the gear mechanism.

As shown in FIGS. 4, 5, 6, 7, and 8, pivot fasteners 20 and 21 pivotally retain the gripper jaws 34 and 35 between the top plate 18 and the bottom plate 19, and are disposed through gripper bores 26 and 27 via fastener bores 22, 24, and 23, and 25 of the top and bottom plates 18, 19, thereby allowing rotation of gripper beveled gears 30 and 31 to pivot the gripper jaws 34 and 35 to any position between fully open and fully closed, like the jaws on a pair of pliers. The gripper beveled gears 30 and 31 are aligned on the bottom plate 19 in a manner that allows their teeth to mesh with the teeth of the first and second elongate arm bevel gears 10 and 11, respectively. As shown in FIGS. 9 and 10, the gear system configuration is such that both first and second elongate arm bevel gears 10 and 11 align perpendicular to the gripper bevel gears 30 and 31. The anterior teeth of both of the first and second elongate arm bevel gears 10 and 11 are in contact with the lateral teeth of the gripper beveled gears 30 and 31. This configuration affects an opening and closing of the jaw sections relative to one another.

The beveled design of the gears 10, 11, 30, and 31 permits teeth rotation of the gripper beveled gears 30 and 31 in response to teeth rotation of the perpendicular first and second elongate arm bevel gears 10 and 11, thereby actuating open-close pivot motion of the grippers 34 and 35 responsive to open-close pivotal motion of the first and second elongate arms 300 and 400 according to finger motion of a user's fingers locked inside of the finger loops 100 and 200. The gear design translates open-close pivoting of the first and second elongate arms 300 and 400 into open-close pivoting of the first and second gripper jaws 34 and 35.

A conventional locking ratchet 500 is attached to the elongate arms 300, 400 near the finger grips 100, 200 and has a detent mechanism that can lock the arms 300, 400 in a user-desired pivotal configuration. The ratchet lock 500 includes two short members attached to and extending between the elongate arms 300, 400. The detent mechanism of the ratchet lock members comprises matching notches on opposing surfaces of the members, which engage one another, locking, as the finger loops are brought together.

The needle holder 7 is preferably constructed of surgical stainless steel. As shown in FIGS. 1 and 2, the surgical needle holder 7 can be adjusted to a fully closed position or to a fully open position. Moreover, the ratcheting mechanism 500 and beveled gear assemblies allow the needle holder 7 to be adjusted to any position in-between fully open and fully closed.

The base plates 28 and 29 of the jaws 34 and 35 have a smaller length, width and height to facilitate connection to the gripper beveled gears 30 and 31 by pins 32 and 33. The actual holder jaws 34 and 35 taper down in both width and height to a terminal, rounded tip as they extend away from the base plates 28 and 29. The pointed tips allow for good directional placement and visualization of needle position by the surgeon using the surgical needle holder 7. As shown in FIG. 8, the gripping surface 203 of the jaw 35 is crosshatched, grooved, or knurled to ensure positive engagement with a curved surgical needle (jaw 34 has the identical pattern gripping surface).

The finger loops 100 and 200 and elongated arms 300 and 400 allow the surgeon to grasp the instrument and apply pressure to close or open the jaws 34 and 35. When the arms 300 and 400 are extended apart at the finger grips 100, 200, the upper (in the drawing) arm 400 will cause the elongate arm gear 10 to move in forward (or downward) motion. This will transmit motion to the gripper jaw gear 30 to move clockwise in order to cause the jaw 34 to open laterally at the pivot pin 20. The motion of the other side will be in the opposite direction. The lower (in the drawing) arm 300 will cause the elongate arm gear 11 to move in backward (or upward) motion. This will transmit motion to the gripper jaw gear 31 to move in a counterclockwise direction, which will cause the jaw 35 to open laterally at pivot pin 21.

The movement is reciprocal in both gears, and therefore having opposite directions of rotation. The elongate arm gears 10 and 11 are capable of movement in a forward and backward direction with respect to the reciprocal movement of the elongated arms 3 and 4 at the pivot joint pin 15. This configuration allows the gripper jaw gears 30 and 31 to rotate in reciprocal movement in clockwise and counterclockwise direction.

Also, the jaw members 34 and 35 are capable of a reciprocal movement about pivot pins 21 and 20. In other words, the jaw members 34 and 35 can move towards and/or away from one another. By applying this gear configuration, the motion of needles will be along any plane parallel to the longitudinal axis of the device.

It is to be understood that the present invention is not limited to the embodiments described above, but encompasses any and all embodiments within the scope of the following claims.

I claim:

1. A surgical needle holder, comprising:
 a first elongate arm having a first annular finger grip at one end and a distal end defining a recess opposite the finger grip;
 a second elongate arm having a second annular finger grip and a distal end defining a recess opposite the second finger grip, the second elongate arm having the same length as the first elongate arm, the first and second annular finger grips being coplanar, the first and second elongate arms bending so that they cross over each other, the first and second elongate arms each having a through bore defined therein;
 a center jaw mount disposed between the ends of the first and second elongate arms distal from the finger grips, the jaw mount having a retaining body defining a through bore, the through bore in the retaining body being aligned with the elongate arm through bores, the retaining body having opposing plates extending therefrom;
 a fastener disposed through the through bores of each elongate arm and the retaining body, the fastener pivotally fastening the first and second elongate arms to the retaining body, thereby establishing scissors action pivotal movement of the first and second elongate arms;

first and second elongate arm gear shafts rigidly attached to the recessed distal ends of the first and second elongate arms, respectively, and first and second elongate arm bevel gears attached to the first and second gear shafts, respectively;

first and second gripping jaws pivotally attached to the opposing plates of the center jaw mount, the gripping jaws each having a base plate extending therefrom, the base plates being smaller in length, width and height than the jaws, the base plates extending between the opposing plates of the center jaw mount, the gripping jaws being adapted for gripping a surgical needle therebetween; and first and second gripping jaw gear shafts rigidly attached to the gripping jaw base plates and first and second gripping jaw bevel gears attached to the first and second gripping jaw gear shafts respectively, the elongate arm gear shafts and the gripping jaw gear shafts extending perpendicular to each other so that the first elongate arm bevel gear and the first gripping jaw bevel gear engage each other at 90°, and the second elongate arm bevel gear and the second gripping jaw bevel gear engage each other at 90°;

wherein pivoting the finger grips in opposite directions pivots the gripping jaws in opposite directions by engagement of the first bevel gears and by engagement of the second bevel gears; and wherein pivoting the finger grips towards each other pivots the gripping jaws towards each other by engagement of the first bevel gears and by engagement of the second bevel gears.

2. The surgical needle holder according to claim 1, further comprising first and second ratchet lock members attached to and extending from said first and second elongate arms, respectively, the ratchet lock members engaging each other to form a ratchet lock when the finger grips are pivoted towards each other in order to lock the surgical needle between the gripping jaws.

3. The surgical needle holder according to claim 1, wherein each said gripping jaw has a gripping surface having a cross-hatched gripping pattern disposed on the gripping surface in order to firmly grip the surgical needle between the gripping jaws.

* * * * *